United States Patent [19]
Garito et al.

[11] Patent Number: 5,683,387
[45] Date of Patent: Nov. 4, 1997

[54] ELECTROSURGICAL ELECTRODE FOR SKIN GRAFTING

[76] Inventors: Jon C. Garito; Alan G. Ellman, both of 1135 Railroad Ave., Hewlett, N.Y. 11557

[21] Appl. No.: 593,010

[22] Filed: Jan. 29, 1996

[51] Int. Cl.$^6$ ................................................. A61B 17/39
[52] U.S. Cl. ................................................ 606/45; 606/41
[58] Field of Search ............................... 606/41, 45, 49

[56] References Cited

U.S. PATENT DOCUMENTS 3,412,732  11/1968  Simon.
4,221,222  9/1980  Detsch.
5,324,288  6/1994  Billings et al. .................... 606/45

FOREIGN PATENT DOCUMENTS 0419235  3/1991  European Pat. Off. ............... 606/45

OTHER PUBLICATIONS

Goldstein, "Esthetics In Dentistry", J.B. Lipincott Co., 1976, pp. 269–271.
Stegman et al., "Basics of Dermatoligic Surgery", Year Book Medical Publ. Inc., 1982, pp. 99–102.

*Primary Examiner*—Lee S. Cohen

[57] ABSTRACT

An electrode for use in an electrosurgical skin grafting procedure. In a preferred embodiment, the electrode is uniquely configured to form a U-support terminating in an active wire, generally U-shaped, whose width controls the width of the graft, and the length of whose arms controls the thickness of the graft. The active wire is supported by structure that is completely electrically-insulated to ensure excision only of the desired tissue while avoiding damage to surrounding tissue. The tissue incising is effected with the bare active wire at a depth stopped by a shoulder between the bare wire arms and the adjacent portions of the electrode support.

16 Claims, 1 Drawing Sheet

ELECTROSURGICAL ELECTRODE FOR SKIN GRAFTING

BACKGROUND OF THE INVENTION

A surgical instrument for removing a skin graft is often called a dermatome. See, for example, U.S. Pat. No. 3,412,732, whose contents are herein incorporated by reference. The more popular dermatomes comprise a frame with an oscillating knife whose position relative to a slot in the frame base may or may not be adjustable to control the thickness of the skin graft. The typical thickness of a skin graft is about 2 mm. The surgeon has to exercise great care to remove a skin section of uniform thickness and with well-defined edges so that the graft fits properly in its recipient bed and with acceptable cosmesis. The conventional procedure can lead to pain and excessive bleeding, especially if the incision depth exceeds about 2 mm.

A simpler form of cutting instrument is described in U.S. Pat. No. 4,221,222, whose contents are herein incorporated by reference. This instrument, which has no moving pans, also uses a sharp edge for cutting into the tissue, and also depends upon the skill of the physician to control the thickness of the resultant graft.

SUMMARY OF THE INVENTION

An object of the invention is an improved skin grafting surgical procedure using an electrosurgical instrument.

We have invented a novel electrode for use in an electrosurgical skin grafting procedure. This electrosurgical procedure using our novel electrode enables physicians to offer to patients a treatment that is efficiently performed, easily learned and thus performed at a significantly reduced price, and with less tissue damage and bleeding compared to procedures done with a knife or blade.

The procedure using our novel electrode is based on performing essentially the same kind of skin excisions as was used heretofore but, in accordance with a feature of our invention, the structure of our novel electrosurgical electrode used to make the excision prevents the excision depth from exceeding a safe value.

In accordance with another feature of our invention, the electrode of the invention is uniquely configured to form an active thin wire, generally U-shaped, whose width controls the width of the graft, and the length of whose arms controls the thickness of the graft. The active wire is supported by structure that is completely electrically-insulated to ensure excision only of the desired tissue while avoiding damage to surrounding tissue, and to allow the physician to use these inactive insulated parts to help position and guide the active wire portion, which is the only part capable of incising tissue, during the surgical procedure. The electrosurgical procedure has the important advantage of being able to cut the tissue with minimum surgeon pressure while at the same time coagulating the cut tissue causing minimum bleeding. It is preferred that the electrosurgical currents used be above 2 MHz, and preferably above 3 MHz. At these high frequencies, commonly referred to as radiosurgery, cutting is accomplished by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

Figure 1:
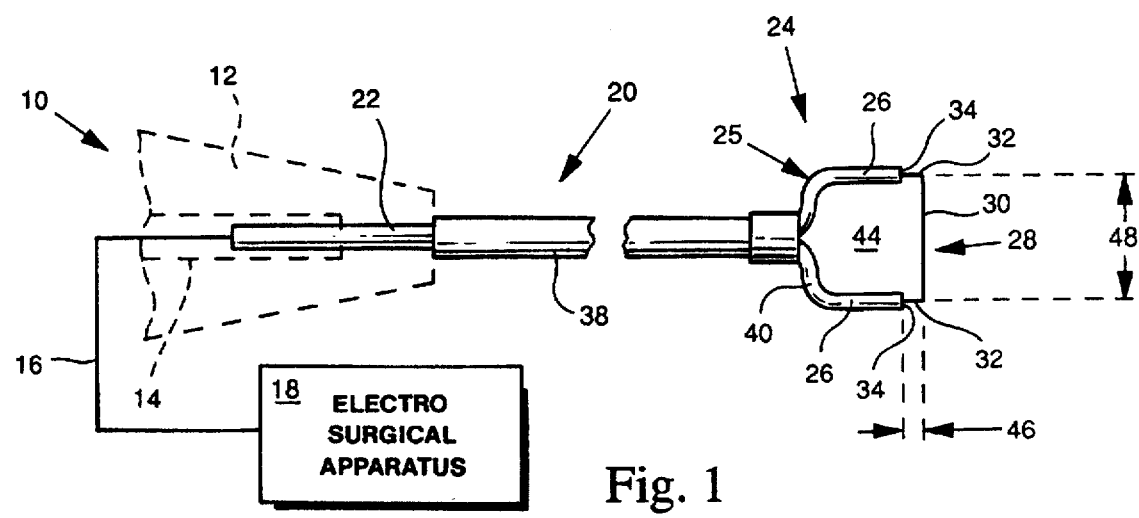
FIGS. 1 is a plan view of one form of electrosurgical instrument in accordance with the invention, shown connected to electrosurgical apparatus.

FIG. 1 illustrates a preferred form of the novel electrosurgical instrument 10 of the invention. It comprises an elongated conventional handpiece 12 (only the collet end is shown in phantom) of electrically-insulating material having a central electrically-conductive tube or conductor 14 extending throughout its length and connected at its end to a cable 16 which is connected in the conventional manner to conventional electrosurgical apparatus 18. As an example only, the electrosurgical apparatus can be model AAOP Surgitron FFPF available from Ellman International, Inc. of Hewlett, N.Y. The Ellman equipment is preferred due to its high operating frequency, typically above 2 MHz, preferably above 3 Mhz. This particular apparatus provides electrosurgical currents at 3.8 MHz.

At the opposite end of the handpiece 12 is mounted an electrosurgical electrode 20 which comprises an electrically-conductive straight axial brass rod 22 running lengthwise through it and mounted at its end nearest the handpiece 12 in the handpiece collet and thus electrically connected to the electrically-conductive tube 14. The distal end of the electrode comprises an electrically-conductive, generally U-support 24 whose bight end 25 is electrically connected to the brass rod 22. Each of the arms 26 of the U-support 24 are connected, as by soldering or welding, to a bare tungsten wire 28. The latter is also U-shaped with a straight bight portion 30 and two arms 32 extending at right angles to the bight portion 30 which are connected to and supported by the arms 26 of the U-support 24. Also connected to the electrosurgical apparatus 18 is the usual indifferent plate (not shown) which during use is in contact with a patient's body. When the electrosurgical apparatus 18 is energized, high frequency electrosurgical currents are generated which are coupled by way of the cable 16, electrically-conductive tube 14, and electrically-conductive rod 22 to the active, bare wire 28. The physician, in the usual way, holds the handpiece 12 while applying the active working end 28 of the electrode to the desired area of the patient to be treated.

In accordance with a feature of the invention, the active electrode portion 28 comprises a thin wire, for example, 0.004 inches in diameter of tungsten. The wide straight part 30 when activated penetrates into the tissue at the donor site to the full depth of the bare arms 32. When activated, the active wire 28 cuts cleanly and easily with little pressure required through the tissue. The wide bottom part 30 forms the base of a rectangular slab of tissue that can be excised and whose width is determined by the length of the transverse (transverse to the longitudinal dimension of the electrode 20) wire part 30 (the vertical dimension in FIG. 1), and whose thickness is determined by the length of the transverse wire arms 32 in the direction parallel to the longitudinal dimension of the electrode (horizontal in FIG. 1). The wide thin wire part 30 helps produce a tissue slab with a base having a generally flat surface and the arms 32 of equal length help ensure that the slab sides are generally straight and parallel, the arms 32 being of equal length ensures that the tissue slab will be of uniform thickness.

The thinner active wire arms 32 form, where each meets the wider electrically-insulated support arms 26, a shoulder 34 which acts as a stop when the active wire 30, 32 is inserted into tissue during the procedure. Electrically-insulated electrode sections which cannot contribute electrosurgical currents cannot cut tissue. With a size of the tungsten wire of, for example, 0.001 mm (=0.004 inches), and a typical diameter of the insulated support arms 26 of about 1 mm, a shoulder 34 is formed having a radius of about 0.45 mm, which is sufficient to prevent tissue penetration exceeding the length of of the wire arms 32. That length is preferably set at 2 mm so that the tissue slab thickness will have about the same value. The area designated 44 inside of the rectangular loop formed by the active wire portions 30, 32 and the U-arms 26 and U-bight 25 is deliberately left empty, for several reasons. When the active wire end 30 of the electrode is inserted into the tissue up to the stops 34, the cutting begins by pulling the electrode along the skin. The tissue slab as it becomes excised passes upward through the clear loop area 44 and then is typically grasped with forceps and lifted clear so the surgeon can clearly see without any obstacles the cutting site from both sides and the manner in which the cutting is occurring to ensure a uniform excision.

In accordance with a further feature of the invention, the arms 26 and bight portion 25 of the U-support 24 as well as the the remaining part of the electrode shaft 20 up until it joins the bare end 22 is covered with a coating of an electrically-insulating material. The coating 38 for the straight shaft part of the electrode may be one of many suitable electrically-insulating rubber or plastic materials. The coating 40 on the U-support 24 comprises a thinner coating of an electrically-insulating material, which may be one of many suitable thin electrically-insulating plastics, baked Teflon being one example. Thus, the entire length of the electrode 20 from the bare active wire end 28 to the bare end 22 which is mounted in the handpiece 12 is electrically insulated from the patient. The handpiece 12, too, is completely electrically-insulated.

The shape of the active wire end 28 with a generally straight transverse portion 30 extending across and between the fight angle side wire portions 32 is critical to achieve the desired object, which is to allow the physician to apply the electrode portion 28 to the tissue at the donor site, activate the apparatus and with relative ease penetrate the region with the bare wire 30,32 up to the dual stops 34, and then move the instrument in the required straight path to make the desired straight incision without fear of exceeding a safe depth of penetration. The insulating coatings 38 and 40 are essential to prevent accidental burning or other tissue damage by the sides of the electrode as the instrument is manipulated over the skin of the patient.

As mentioned, preferably the length 46 of the longitudinal active wire portions 32 is 2 mm to obtain a 2 mm thick slab. If desired, the length of the wire portions 32 can be increased to 3 mm for a thicker slab, or reduced to 1 mm for a thinner slab. The slab width is determined by the spacing between U-arms 26, indicated by the reference numeral 48. Preferably, with the U-arms 26 parallel, that spacing is 10 mm for a 10 mm wide slab. The configuration of the active end lends itself to the manufacture of a family of electrodes capable of providing grafts of various thicknesses and widths. For example, the same configuration as illustrated in FIG. 1 but with active wire portions 32 of different lengths, say from 1–3 mm, will provide a first family of electrodes capable of providing grafts of the same width but with different thicknesses.

Figure 2:
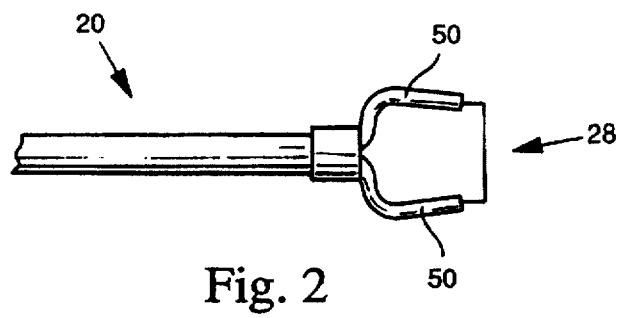
FIGS. 2, 3 and 4 are plan views of variants of the electrosurgical instrument according to the invention.
Figure 3:
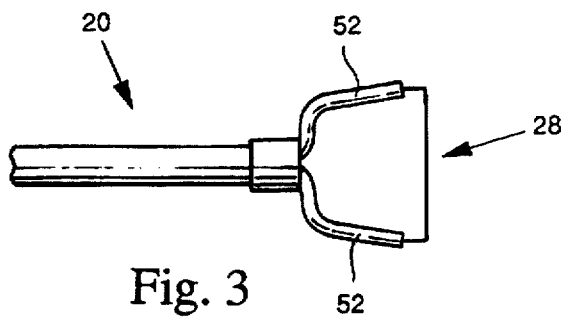

FIGS. 2 and 3 show modified configurations for providing grafts of different widths to provide a second family of electrodes. For instance, the configuration of FIG. 2, by bending inward the free ends 50 of the U-arms, provides an active wire width of 8 mm. Similarly, the configuration of FIG. 3, by bending outward the free ends 52 of the U-arms 26, provides an active wire width of 12 mm. In both cases, the electrodes are otherwise the same.

Figure 4:
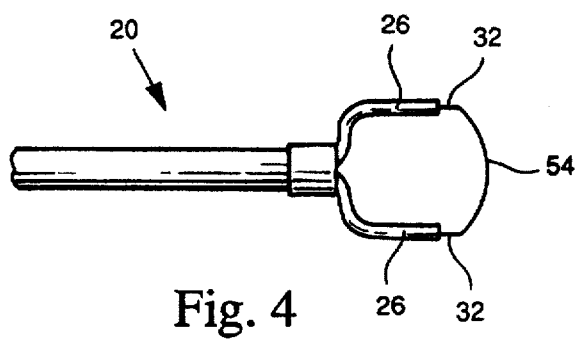

Occasionally, it becomes desirable to obtain a graft from the palate in the throat, which is especially suitable for grafts along the gums of a patient. The palate is slightly bowed inward, concave when viewed from the mouth. In such a case, to obtain a skin graft with uniform thickness from the concave palate or other similarly curved tissue, it is desirable to use an active wire shape that is complementary to that of the palate. This is easily achieved, as is illustrated in FIG. 4, by a slight bowing 54 of the active wire bight portion, with the remaining parts of the electrode remaining the same. A 0.004 inches wire of tungsten is sufficiently stiff to hold the bowed shape imparted to it during manufacture. A typical bowing radius is about 0.3–0.6, preferably about 0.4, inches. Hence, with relative ease, the family of electrodes can be enlarged to include several sizes of electrodes with bowed active wire portions for use with donor sites that are curved.

With the Ellman equipment, the fully rectified or cut/coag current is used at a power setting of about 3–4 with the active bare wire electrode 28. There is very little trauma and the sore area felt by the patient at the donor site is easily handled by analgesia and anti-inflammatory drugs.

It will also be understood that the electrode of the invention is not limited to its use for a skin grafting procedure. To those skilled in this art, there will certainly be other uses for this novel electrode that provides a U-shaped active wire tip, with adjacent electrode sections coated with insulating material for accurately guiding and controlling the position of the active tip during a tissue incising electrosurgical procedure.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode for excising a thin slice of skin tissue for skin grafting, comprising:

(a) an electrically-conductive shaft member having a first end for mounting to a handpiece and a second end, (b) said second end comprising an active, electrically-conductive, wire portion having a generally U-shape formed by exposed arm portions extending in a longitudinal direction and on opposite sides of an exposed bight portion extending substantially transversely to the longitudinal direction, said bight portion being straight or slightly bowed, (c) said active wire portion being exposed electrically for applying electrosurgical currents to said tissue when said shaft member is connected to a source of electrosurgical currents, (d) said shaft member having portions adjacent said exposed arm portions, said shaft portions being electrically-insulating to prevent contact and passage of electrosurgical currents to areas adjacent to or surrounding the tissue to be excised, said active wire portion being configured such that the thickness and width of the skin tissue slice excised is determined by the length in the longitudinal direction of the exposed arm portions and the length of the exposed bight portion extending substantially transversely thereto.

2. An electrosurgical electrode as claimed in claim 1, wherein the arm portions of said active wire portion having a length in the longitudinal direction not exceeding about 3 mm.

3. An electrosurgical electrode as claimed in claim 1, wherein said second end of said shaft member comprises a generally electrically-insulating U-support comprising a bight portion and two arm portions each connected to one of the arm portions of the active wire portion.

4. An electrosurgical electrode as claimed in claim 3, wherein the two arm portions of said electrically-insulating U-support adjacent the arm portions of said active wire portion have a larger diameter than that of said arm portions of said active wire portion forming with each of the latter a shoulder acting as a stop preventing tissue penetration of the active wire portion beyond the length of its arm portions.

5. An electrosurgical electrode as claimed in claim 4, wherein the bight portion of the active wire portion has a length transverse to the longitudinal direction between about 8–12 mm.

6. An electrosurgical electrode as claimed in claim 5, wherein the bight portion of the active wire portion is straight.

7. An electrosurgical electrode as claimed in claim 5, wherein the bight portion of the active wire portion is slightly concave viewed from the shaft member.

8. An electrosurgical electrode as claimed in claim 5, wherein the bight portion of the active wire portion is constituted of a thin wire having a diameter of about 0.004 inches.

9. An electrosurgical electrode as claimed in claim 3, wherein the active wire portion and the electrically-insulating U-support form a generally rectangular open loop.

10. The electrosurgical electrode as claimed in claim 1, wherein the active wire portion is made of tungsten.

11. The electrosurgical electrode as claimed in claim 10, wherein the active wire portion of tungsten has a diameter of about 0.004 inches.

12. The electrosurgical electrode as claimed in claim 1, wherein the arm portions of the active wire portion have a length of 1–3 mm.

13. In combination:

electrosurgical apparatus capable of supplying high frequency currents, a handpiece having means at one end for connection to the electrosurgical apparatus and having at its opposite end means for mounting the electrically-conductive shaft member of an electrosurgical electrode and for supplying the high frequency currents to said electrode;

an electrosurgical electrode for excising a thin slice of skin tissue for skin grafting, comprising:
(a) an electrically-conductive shaft member having a first end for mounting to the handpiece and a second end,
(b) said second end comprising an active, electrically-conductive, wire portion having a generally U-shape formed by exposed arm portions extending in a longitudinal direction and on opposite sides of an exposed bight portion extending substantially transversely to the longitudinal direction, said bight portion being straight or slightly bowed,
(c) said active wire portion being exposed electrically for applying electrosurgical currents to said tissue when said shaft member is connected to the electrosurgical apparatus,
(d) said shaft member having portions adjacent said exposed arm portions, said shaft portions being electrically-insulating to prevent contact and passage of electrosurgical currents to areas adjacent to or surrounding the tissue to be excised,
(e) means forming a shoulder where said exposed arm portions meet the adjacent portions of said shaft member, said shoulder being sufficiently wide to prevent tissue penetration of said active wire portion beyond its length in the longitudinal direction of the arm portions, said active wire portion being configured such that the thickness and width of the skin tissue slice excised is determined by the length in the longitudinal direction of the arm portions and the length of the bight portion extending between the arm portions.

14. The combination of claim 13, wherein the high frequency currents are at a frequency exceeding 2 Mhz.

15. A skin graft surgical procedure for excising tissue of a patient, comprising the steps:
(a) providing electrosurgical apparatus connected to a handpiece holding an electrosurgical electrode, said electrosurgical electrode comprising:
(i) an electrically-conductive shaft member having a longitudinal direction and a first end for mounting to the handpiece and a second end,
(ii) said second end comprising an active, electrically-conductive, wire portion having a generally U-shape formed by exposed arm portions on opposite sides of an exposed bight portion,
(iii) said active wire portion being exposed electrically for applying electrosurgical currents to said tissue when said shaft member is connected to the electrosurgical apparatus,
(iv) said shaft member having portions adjacent said exposed arm portions, said shaft member portions being electrically-insulating to prevent contact and passage of electrosurgical currents to areas adjacent to or surrounding the tissue to be excised,
(v) means forming a shoulder where said active wire portion meets the adjacent portions of said shaft member, said shoulder being sufficiently wide to prevent tissue penetration of said active wire portion beyond its length,
(b) applying the active wire portion of the electrode to a donor site of a patient for the graft and activating the electrosurgical apparatus,
(c) penetrating the tissue of the patient until stopped by the means forming a shoulder,
(d) excising a graft with the active wire portion of the electrode by moving the electrode through the tissue.

16. The skin graft surgical procedure of claim 15 wherein the electrosurgical currents are at a frequency exceeding 2 MHz.

* * * * *